(12) United States Patent
Reiss et al.

(10) Patent No.: US 7,424,323 B1
(45) Date of Patent: Sep. 9, 2008

(54) IMPLANTABLE CARDIAC STIMULATION DEVICE PROVIDING AUTOCAPTURE WITH PMT AVOIDANCE AND METHOD

(75) Inventors: Josh Reiss, Sunnyvale, CA (US); Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 342 days.

(21) Appl. No.: 11/218,770

(22) Filed: Sep. 1, 2005

(51) Int. Cl.
*A61N 1/362* (2006.01)

(52) U.S. Cl. .............................. 607/9; 607/14
(58) Field of Classification Search ........... 607/9, 607/14, 27
See application file for complete search history.

(56) References Cited

U.S. PATENT DOCUMENTS

| | | | |
|---|---|---|---|
| 5,861,007 A * | 1/1999 | Hess et al. ................ | 607/9 |
| 6,243,606 B1 | 6/2001 | Mann et al. ............... | 607/14 |
| 6,259,950 B1 | 7/2001 | Mann et al. ............... | 607/28 |
| 6,263,244 B1 | 7/2001 | Mann et al. ............... | 607/28 |
| 6,285,908 B1 | 9/2001 | Mann et al. ............... | 607/28 |
| 6,584,354 B1 | 6/2003 | Mann et al. ............... | 607/28 |
| 6,618,622 B1 | 9/2003 | Mann et al. ............... | 607/28 |

OTHER PUBLICATIONS

Paul A. Levine, MD, "Postventricular Atrial Refractory Periods and Pacemaker Mediated Tachycardias", *Clin. Prog. In Pacing and Electrophysiol.*, vol. 1, No. 4 (1983), pp. 394-401.

\* cited by examiner

*Primary Examiner*—Kennedy J Schaetzle

(57) ABSTRACT

An implantable cardiac stimulation device prevents pacemaker mediated tachycardias during autocapture. The device includes a refractory circuit that establishes a lengthened post ventricular atrial refractory period (PVARP) in response to a lengthened AV interval. Such a lengthened AV interval may occur as a result of the provision of a back-up pacing pulse or fusion beat evaluation during autocapture.

17 Claims, 5 Drawing Sheets

IMPLANTABLE CARDIAC STIMULATION DEVICE PROVIDING AUTOCAPTURE WITH PMT AVOIDANCE AND METHOD

FIELD OF THE INVENTION

The present invention generally relates to an implantable cardiac stimulation device that provides electrical therapy to a patient's heart. The present invention more particularly relates to such a device that supports automatic capture threshold assessment while providing PMT avoidance through post ventricular atrial refractory period (PVARP) adjustment to compensate for extended AV intervals caused by back-up pulses and fusion beat evaluation.

BACKGROUND

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered as a pacing system. The pacing system is comprised of two major components. One component is a pulse generator which generates the pacing stimulation pulses and includes the electronic circuitry and the power cell or battery. The other component is the lead, or leads, having electrodes which electrically couple the pacemaker to the heart. A lead may provide both unipolar and bipolar pacing and/or sensing electrode configurations. In the unipolar configuration, the pacing stimulation pulses are applied or intrinsic responses are sensed between a single electrode carried by the lead, in electrical contact with the desired heart chamber, and the pulse generator case. The electrode serves as the cathode (negative pole) and the case serves as the anode (positive pole). In the bipolar configuration, the pacing stimulation pulses are applied or intrinsic responses are sensed between a pair of closely spaced electrodes carried by the lead, in electrical contact with the desired heart chamber, with the most proximal electrode serving as the anode and the most distal electrode serving as the cathode.

Pacemakers deliver pacing pulses to the heart to induce a depolarization of that chamber and this is followed by a mechanical contraction of that chamber when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses in one chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode. Recently, there has been the introduction of pacing systems that stimulate in multiple sites in the same chamber or in both the right and left ventricles or atria. These are termed multisite stimulation systems. Whenever we refer to dual chamber pacing, it will be inferred that multisite systems are included.

The energies of the applied pacing pulses must be above the pacing energy stimulation or capture threshold of the respective heart chamber to cause the heart muscle of that chamber to depolarize. If an applied pacing pulse has an energy below the capture threshold of the respective chamber, the pacing pulse will be ineffective in causing the heart muscle of the respective chamber to depolarize or contract. As a result, there will be failure in sustaining the pumping action of the heart. It is therefore necessary to utilize applied pacing pulse energies which are assured of being above the capture threshold.

Capture thresholds are assessed at periodic follow-up visits with the physician and the output of the pacemaker may be adjusted (programmed) to a safety margin that is appropriate based on the results of that evaluation. However, capture thresholds may change between scheduled follow-up visits with the physician. A refinement of the technique of periodic capture threshold measurement by the physician is the beat-by-beat monitoring of capture, delivery of a higher output back-up pulse when there is failure to recognize capture and automatic performance of capture threshold assessment and the automatic adjustment of the output of the pulse generator. This entire process is termed autocapture.

As is well known in the art, the capture threshold of a heart chamber can, for various reasons, change over time. Hence, pacemakers that incorporate autocapture are generally able to periodically and automatically perform autocapture tests. In this way, the variations or changes in capture threshold can be accommodated.

When a pacing pulse is effective in causing depolarization of the heart muscle, it is referred to as "capture" of the heart. Conversely, when a pacing pulse is ineffective in causing depolarization of the heart muscle, it is referred to as "lack of capture", "loss of capture" or "non-capture" of the heart. These terms should be considered synonyms and will be used interchangeably in this discussion.

In one known autocapture test, the pulse generator applies a succession of primary pacing pulses to the heart at a basic rate. To assess the threshold, the output of the primary pulse is progressively reduced. The output of each successive pair of primary pacing pulses is reduced by a known amount and capture is verified following each pulse. If a primary pulse results in loss of capture, a higher output backup or safety pulse is applied to sustain heart activity. If two consecutive primary pulses at the same output level result in loss of capture, the system identifies that output as being below the threshold and then starts to increment the output of the primary pulse. The output of successive primary pacing pulses is then incrementally increased until a primary pacing pulse regains capture. The output of the primary pulse which regains capture is the capture threshold to which a working margin is added in determining the pacing energy.

Delivery of a back-up pulse is normally provided about 60-100 milliseconds after the primary pulse which failed to capture the heart tissue. This effectively lengthens the normal AV interval by the 60-100 milliseconds. As used herein the term "AV interval" is meant to refer to the time interval beginning with an atrial event, either an atrial pacing pulse or an intrinsic P wave, and ending with the next scheduled ventricular pacing pulse. Hence, when the heart fails to respond to a primary pacing pulse with an evoked response, the normal AV interval of, for example, 150-250 milliseconds is extended for delivery of the back-up pulse 60-100 milliseconds later. Therefore, as far as the heart is concerned, the effective lengthened AV interval can be, for example, a minimum of 210 milliseconds and a maximum of 350 milliseconds with the exemplary interval ranges previously mentioned. During the extended functional AV interval, between an atrial event and the delivered back-up ventricular output, the atrium may have recovered on a physiologic basis to allow retrograde conduction to occur and the initiation of a pacemaker mediated tachycardia (PMT).

Another condition which may occur during autocapture is a fusion beat. A fusion beat occurs when a paced evoked response occurs essentially simultaneously with an intrinsic R wave. The result may be an attenuation of the evoked response signal amplitude to a value that is below the ER Sensitivity setting. If this happens, fusion which is associated with a myocardial depolarization will not be recognized and will be labeled "loss of capture." There is an algorithm designed to screen for fusion since the presence of fusion implies intact AV nodal conduction. On the cycle following that first loss of capture associated with the primary pulse, the AV interval for the next cardiac cycle is lengthened by 100 to 120 ms. If conduction is intact, this extended AV delay will allow conduction to occur, the conducted QRS complex to be sensed and the ventricular output to be inhibited. This lengthened AV interval may also allow the atria to physiologically recover to allow a retrograde P wave to occur and the initiation of a PMT on the "fusion avoidance" cycle of the Auto-Capture algorithm. A PMT results when the device detects a P-wave induced by retrograde conduction following either a native or paced ventricular complex in the atrial alert period, namely after completion of the Post-Ventricular Atrial Refractory Period (PVARP). When this occurs, the pacemaker subsequently, after a sensed AV interval and possible extension of that interval associated with the maximum tracking rate timing circuit, initiates a paced ventricular beat. Repeated stimulation at a high rate is sustained by heart tissue retrograde conduction and by pacemaker anterograde conduction.

Methods for preventing PMT are well known in the art. One such known method involves the use of programmable post-ventricular atrial refractory periods (PVARP), where the PVARP is programmed to be longer than the retrograde conduction interval. The downside of a long PVARP is that it limits the maximum allowed pacing rate. Another known method is based on the fact that the majority of PMTs are initiated by ventricular premature beats defined as an intrinsic ventricular event that is not preceded by an atrial beat. Thus, in this method, a ventricular premature beat causes a prolonged PVARP while the PVARP in other circumstance can be short thus allowing a higher maximum tracking rate. Still another method is to trigger a simultaneous atrial stimulation with a ventricular premature beat causing the atrium to be refractory precluding retrograde conduction from occurring. While the foregoing preventive measures are appropriate to prevent most PMTs triggered by a premature ventricular contraction or atrial undersensing as the conducted QRS will also be labeled a PVC. However, atrial undersensing followed by delivery of an atrial output with functional loss of atrial capture, true loss of atrial capture, upper rate behavior with sensed AV interval extension and other unique situations which may allow for retrograde conduction and thus precipitate a PMT during autocapture will not be able to handled by the unique PVC algorithms. One of these unique situations is true loss of ventricular capture associated with the primary pulse resulting in a functional extension of the AV delay created by delivery of the back-up pulse associated with the AutoCapture algorithm. The present invention addresses these issues.

SUMMARY

What is described herein is an implantable cardiac stimulation system including a pulse generator that provides atrial and ventricular pacing stimulation pulses and a sensing circuit that provides atrial and ventricular sensing. The device comprises a timing control circuit that establishes an AV interval from an atrial event to provision of a ventricular pacing pulse, and a refractory circuit that establishes a PVARP following each provided ventricular pacing pulse including a lengthened PVARP greater in duration than a normal PVARP responsive to the timing control circuit establishing a lengthened AV interval greater in duration than a normal AV interval.

The refractory circuit may establish the lengthened PVARP by providing a second PVARP initiated during a first PVARP or an extension of the first PVARP. The second PVARP may be longer in duration than the first PVARP.

The refractory circuit may initiate the second PVARP responsive to a back-up ventricular pacing pulse being delivered during the first PVARP.

The device may further comprise an evoked response detector that detects loss of capture by a primary ventricular pacing pulse. The functionally lengthened AV interval may then extend from an atrial event to a back-up ventricular pacing pulse.

The device may further comprise a detection algorithm to recognize fusion beats. The timing control circuit may then establish the lengthened AV interval responsive to detection of a fused beat with an extension of the PVARP associated with the ventricular event terminating the extended AV delay.

The refractory circuit may terminate the PVARP responsive to the sensing circuit sensing a P wave during the lengthened PVARP. The pulse generator may then provide an atrial pacing pulse a fixed time after sensing of the P wave.

The pulse generator may provide an atrial pacing pulse a fixed interval after the lengthened PVARP.

The atrial timing circuit may further provide an atrial alert period following the lengthened PVARP independent of the originally programmed base rate or sensor-driven rate at that time. The pulse generator may then provide an atrial pacing pulse upon completion of the atrial alert period.

The timing control circuit may further time a VA interval to schedule provision of a next atrial pacing pulse. The pulse generator may then provide an atrial pacing pulse a fixed interval after detection of a retrograde P wave by the sensing circuit during the lengthened PVARP when the time between the retrograde P wave and the scheduled atrial pacing pulse is less than a present duration.

The present invention still further provides a method for use in an implantable cardiac stimulation device including a pulse generator that provides atrial and ventricular pacing stimulation pulses and a sensing circuit that provides atrial and ventricular sensing. The method comprises timing an AV interval from an atrial event to provision of a ventricular pacing pulse, and establishing a lengthened PVARP greater in duration than a normal PVARP responsive to the timing of a lengthened AV interval greater in duration than a normal AV interval.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
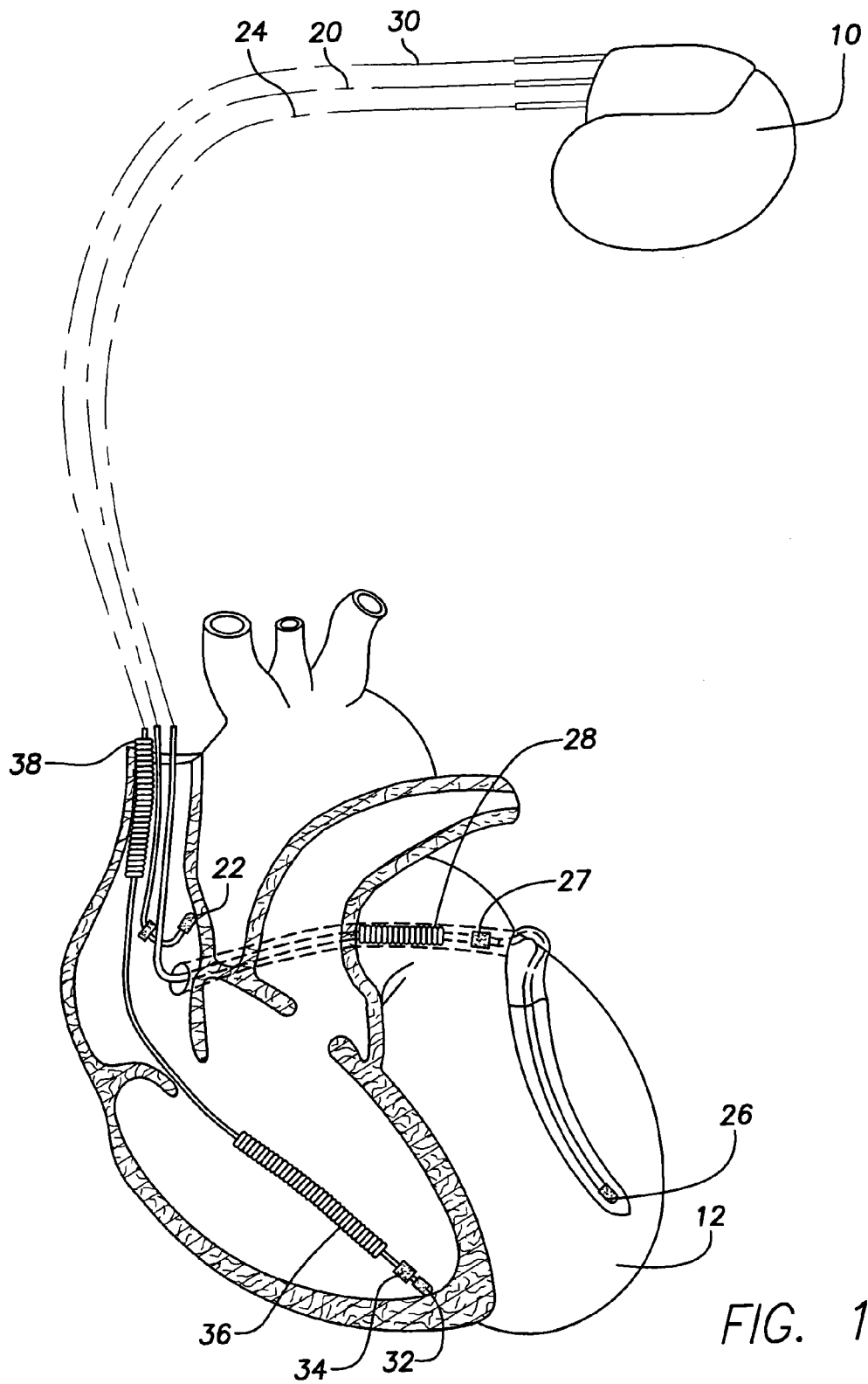
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
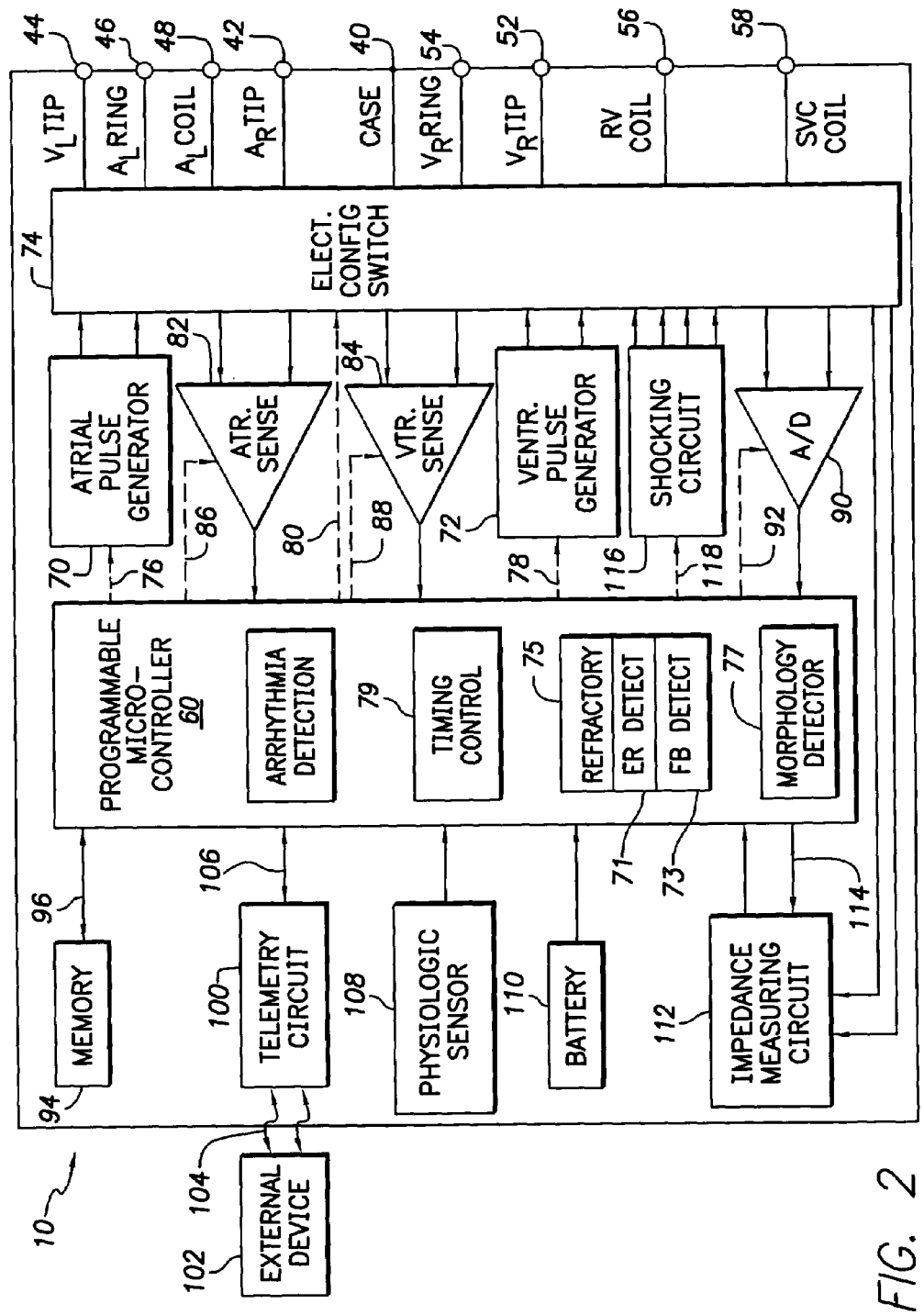
FIG. 2 is a functional block diagram of the implantable stimulation device of FIG. 1 illustrating an embodiment of the present invention.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller or processor 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) interval or delay, ventricular-atrio (VA) interval or delay, atrial interconduction (A-A) delay, or ventricular interconduction (V-V) delay, etc.) as well as to keep track of the timing of blanking intervals, noise detection windows, evoked response windows, alert intervals, marker channel timing, etc., which is well known in the art. The microcontroller 60 also includes a refractory circuit 75. The refractory circuit 75 times refractory periods, including post ventricular atrial refractory periods (PVARP) as described subsequently.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., brady-cardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, in embodiments described herein, the data acquisition system 90 may be coupled to the microcontroller, or other detection circuitry, such as an evoked response detector (ERDETECT) 71, for detecting an evoked response from the heart 12 in response to an applied stimulus, thereby aiding in the detection of "capture". Capture occurs when an electrical stimulus applied to the heart is of sufficient energy to depolarize the cardiac tissue. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection preferably occurs on a beat-by-beat basis associated with the autocapture algorithm. Preferably, the capture threshold search is performed as previously described.

The microcontroller 60 still further includes a fusion beat detector (FBDETECT) 73. The fusion beat detector is provided to determine if a ventricular activation is a true evoked response. If a ventricular activation does not result in a sufficiently large ER signal, capture is not known to have occurred. To help determine if this initial "Loss of Capture" (LOC) complex was due to ER undersensing associated with fusion or true loss of capture, the algorithm extends the AV delay by 100 ms on the next cycle. In the presence of intact AV nodal conduction, the extended AV delay is likely to result in ventricular output inhibition associated with the conducted R wave. As such, the original "LOC" will be ascribed to fusion and there will be no change in the output of the primary pulse. If this was true loss of capture and there was AV block such that there was also LOC on the ventricular output associated with the extended AV delay, then true loss of capture will be diagnosed and the system will initiate its capture recovery algorithm. However, associated with true loss of capture, the functional AV delay will be the programmed AV delay plus fusion assessment extension on the AV delay and the additional interval required to deliver the back-up safety pulse. To evaluate for a true evoked response, the fusion beat detector 73 calls on the morphology detector 77 to compare the ventricular activation as recorded by the data acquisition system to a stored representation of an evoked response. Such morphology comparisons are known in the art.

If loss of capture is detected, the fusion beat detector 71 will cause the timing control 79 to extend the next AV interval to separate the probable timing of an intrinsic R wave from the next scheduled ventricular pacing pulse. As will be seen subsequently, in accordance with embodiments of the present invention, such an AV interval extension or lengthening will cause the refractory circuit 75 to provide a lengthened PVARP to prevent PMT.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries known in the art.

As further shown in FIG. 2, the device 10 is shown as having an impedance measuring circuit 112 which is enabled by the microcontroller 60 via a control signal 114. The known uses for an impedance measuring circuit 120 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 5 joules), moderate (6-15 joules), or high energy (16 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level, i.e., corresponding to thresholds in the range of 16-40 joules. Although external ICDs deliver the shock asynchronously (since R-waves may be too disorganized and small) in the setting of ventricular fibrillation, the implantable devices still synchronize with a ventricular depolarization signal.

Accordingly, the microcontroller 60 is capable of controlling the delivery of the shocking pulses of various energy levels depending on the detected rate and identification of the rhythm by the implanted ICD.

Figure 3:
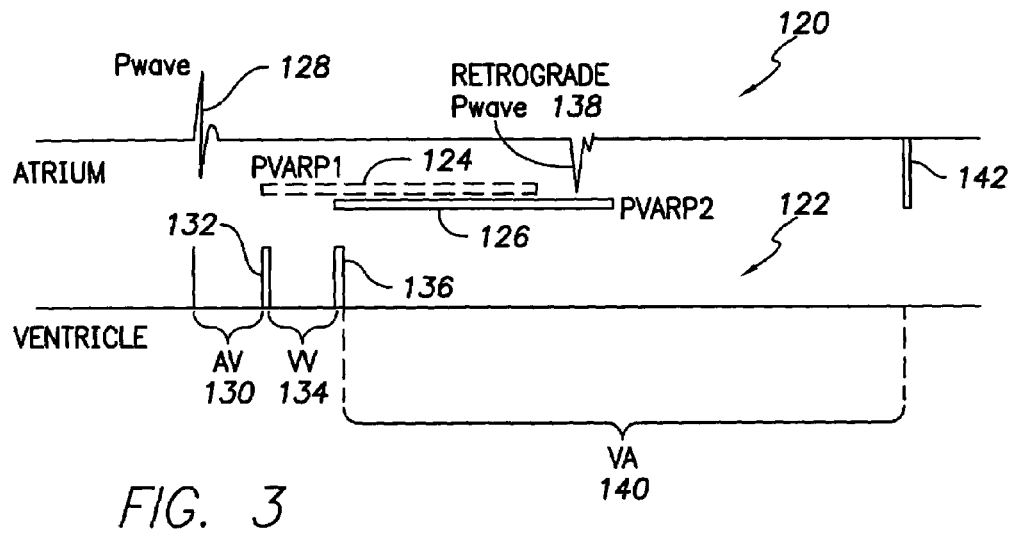
FIG. 3 is a timing diagram illustrating a first back-up pulse embodiment of the present invention.

In FIG. 3, a timing diagram is shown describing the operation of the device 10 in one embodiment of the invention. This timing diagram and the other timing diagrams of FIGS. 4-7 are meant to illustrate embodiments of the invention as may be applied to autocapture.

The timing diagram of FIG. 3 illustrates a back-up pulse embodiment of the present invention and includes an atrial channel 120 and a ventricular channel 122 wherein both the intrinsic and paced events are represented in appropriate chronological order. Also illustrated in FIG. 3 is a first PVARP 124 and a second PVARP 126.

The first activity to note is the sensed P wave 128. The sensed P wave 128 causes the timing control 79 to begin an AV interval 130. At the end of the AV interval 130, the ventricular pulse generator 72 issues a ventricular pacing pulse 132. The issuance of the ventricular pacing pulse 132 causes the refractory circuit 75 to begin timing the first PVARP 124. As previously mentioned, during a PVARP, the device does not respond to any intrinsic atrial activity sensed by the atrial sense amplifier 82 but it still can be detected by the system. Hence, any atrial activation occurring during a PVARP will not be tracked for timing delivery of a next scheduled ventricular pacing pulse.

In accordance with this embodiment, the evoked response detector 71 fails to detect an evoked response to the ventricular pacing pulse 132 and hence requiring delivery of a back-up pulse 136. Accordingly, the timing circuit 79 starts to charge the back-up pulse output capacitor to deliver the back up ventricular stimulus which is the 60-100 millisecond interval from the primary pacing pulse to delivery of the back-up pacing pulse 136. The result is a functional extension of the AV delay comprising the sum of cycles 130 and 134. The back-up pacing pulse 136 is provided with an output of sufficient magnitude to assure capture of the cardiac tissue.

As will also be noted in FIG. 3, when the back-up pulse 136 is delivered, the refractory circuit 75 begins the second PVARP 126 during the first PVARP 124 and identical in length to the first PVARP 124. Hence, the second PVARP 126 functionally lengthens the imposed PVARP comparable to the lengthened AV interval comprising the first and normal AV interval 130 and the functional AV interval extension by the VV interval 134.

Alternatively, to effectively lengthen the PVARP, the refractory circuit 75 may terminate the first PVARP 124 and restart the PVARP with PVARP 126. Instead of having two overlapping PVARP intervals being timed to provide the extended PVARP, serial or immediately successive PVARP intervals may be timed to achieve the PVARP extension.

As may also be noted in FIG. 3, the second PVARP 126 extends past the occurrence of a retrograde P wave 138. The retrograde P wave 138 occurs because the extended AV interval gave the atria sufficient time to physiologically recover and make the atria vulnerable to a retrograde conduction following the ventricular pacing pulse at the end of the markedly extended AV delay. The retrograde P wave 138 will not, however, be tracked by the device because of the lengthened PVARP. In this manner, a potential PMT is avoided.

The next cardiac interval is not initiated until after the timing of a VA interval 140 by the timing control 179. At the end of the VA interval an atrial pacing pulse 142 is delivered to initiate the next cardiac cycle. If an intrinsic P wave had been sensed in the time period between the end of the second PVARP 126 and before the end of the VA interval 140, the pacing pulse 142 would be inhibited. The timing control 79 would terminate the timing of the VA interval 140, and start a new AV interval from the sensed P wave.

As may be noted in FIG. 3, the back-up pulse 136 resulted in a functionally lengthened AV interval. Without the second PVARP 126 and the effective restart of the PVARP with back-up pulse 136, the retrograde P wave 138 following the ventricular depolarization associated with the back-up pulse may have otherwise been sensed as it would have occurred after completion of the PVARP initiated in association with the primary pulse and been tracked to initiate a possible PMT. However, because the PVARP was effectively extended, this retrograde P wave 138 occurred during the extended PVARP, it was not tracked to avoid a possible PMT.

Figure 4:
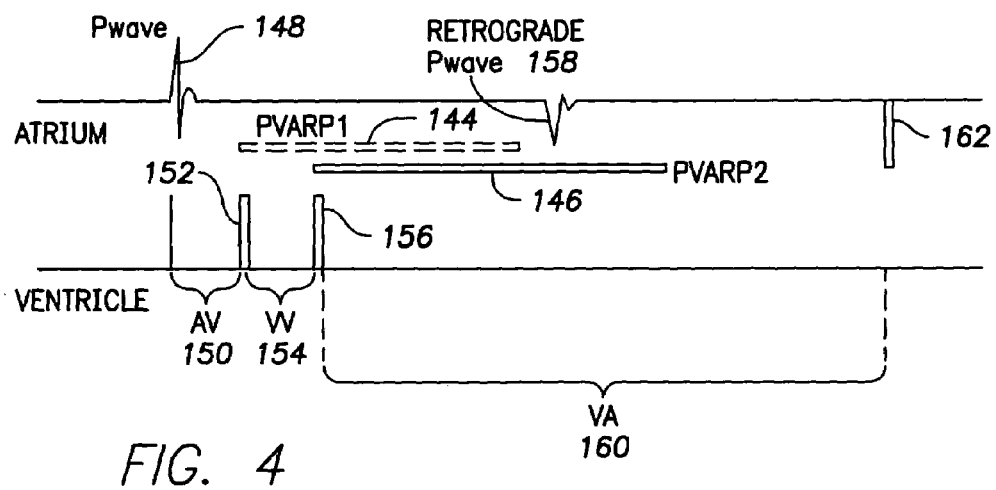
FIG. 4 is a timing diagram illustrating a second back-up pulse embodiment of the present invention.

Referring now to the embodiment of FIG. 4, the timing diagram there illustrated is similar to the timing diagram of FIG. 3. Here it may be seen that a sensed intrinsic P wave 148 causes the timing control 79 to begin timing a first AV interval 150. At the end of the first AV interval 150, the ventricular pulse generator 70 issues a primary pacing pulse 152. With the delivery of the primary pacing pulse 152, the refractory circuit 75 begins the timing of a first PVARP 144.

As illustrated in FIG. 4, the primary pacing pulse 152 was ineffective to capture the cardiac tissue. Accordingly, the evoked response detector 71 fails to detect an evoked response and causes the timing control 79 to begin to charge the back-up pulse output capacitor to deliver the back up ventricular stimulus resulting in a functional extension of the AV interval caused by the additional VV interval 154. At the end of the AV interval extension 154, the ventricular pulse generator 72 delivers a back-up pacing pulse 156. Again, the magnitude of the back-up pacing pulse is selected to assure capture of the cardiac tissue.

Upon delivery of the back-up pulse 156, the refractory circuit 75 starts a second PVARP 146. Here, however, it will be noted that the second PVARP 146 is longer in duration than the first PVARP 144. As a result, it is more probable that if a retrograde P wave does occur following the ventricular capture associated with the back-up pulse, it will coincide with the extended PVARP. Since the retrograde P wave 158 occurred during the extended PVARP, it will not be tracked to prevent a possible PMT. Instead, the timing control 79 times a VA interval from the back-up pulse 156. At the end of the VA interval, the atrial pulse generator 70 delivers an atrial pacing pulse 162. Again, if an intrinsic P wave had occurred after the end of the second PVARP 146 and before the end of the VA interval 160, the atrial pacing pulse 162 would be inhibited and the timing control 79 would begin the timing of a new AV interval from the sensed P wave.

Figure 5:
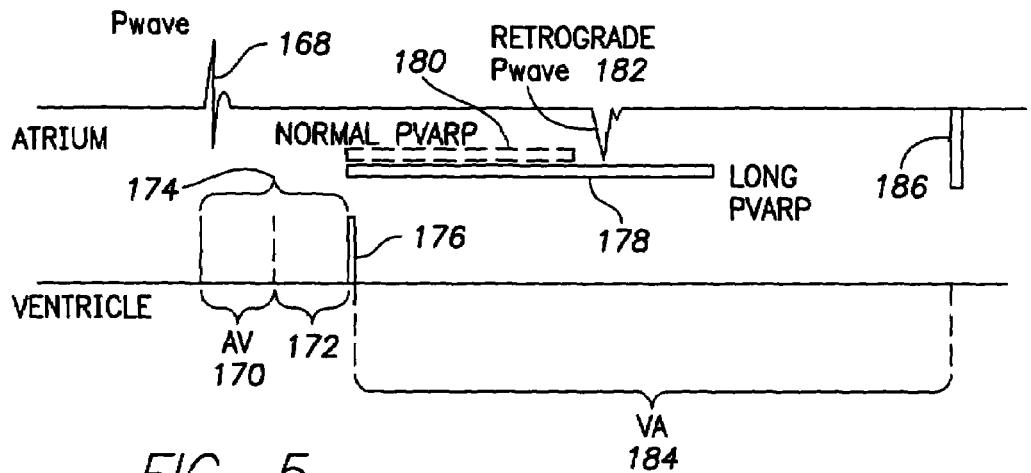
FIG. 5 is a timing diagram illustrating a fusion beat evaluation embodiment of the present invention.

Referring now to FIG. 5, it illustrates a fusion beat evaluation embodiment of the present invention. As shown in FIG. 5, a P wave 168 is detected which causes the timing control 79 to time a first AV interval 170. Here, however, at the end of the first AV interval 170, a ventricular pacing pulse is delivered but because of fusion, capture is not detected and the complex is labeled "loss of capture". The expected back-up pulse is delivered. To determine if the loss of capture on that primary pulse was due to fusion or true loss of capture, FIG. 5 represents the next cycle AFTER the first loss of capture cycle. In this setting, the originally scheduled primary pulse at the end of the AV delay is NOT delivered as diagrammatically represented by a dashed line rather than a thick line. The AV delay is extended by 100 to 120 ms or some other programmable value resulting in delivery of the ventricular output 176. Thus the effective AV delay for this cycle is intervals 170 added to 172.

At the end of the lengthened AV interval 174, the ventricular pulse generator 72 delivers a ventricular pacing pulse 176 if intrinsic AV nodal conduction and a sensed QRS complex had not occurred within the extended interval. In accordance with this embodiment of the present invention, the refractory circuit 75, responsive to the lengthened AV interval 174, provides a PVARP 178 which is longer in duration than a normal PVARP. Such a normal PVARP is represented by the dashed lines 180 in FIG. 5.

After the ventricular pacing pulse 176 results in ventricular capture, a retrograde P wave 182 occurs. As will be noted, the retrograde P wave 182 occurs during the lengthened PVARP 178. As a result, the retrograde P wave 182 is not tracked by the device to set up a potential PMT.

In contrast, had the refractory circuit 175 provided a PVARP of normal length such as PVARP 180, the retrograde P wave 182 would have occurred thereafter to permit the retrograde P wave to be sensed and tracked. The result would be the setting up of a potential PMT. However, by virtue of the lengthened PVARP 178, a potential PMT is avoided.

As will also be noted in FIG. 5, the ventricular pacing pulse 176 initiates the timing of a VA interval 184 by the timing control 79. At the end of the VA interval 184, the atrial pulse generator 70 delivers an atrial pacing pulse 186 to initiate a next cardiac cycle. As in the previous embodiments, should an intrinsic P wave be sensed and detected after the lengthened PVARP 178 and before the end of the VA interval 184, the sensed P wave would be tracked and the atrial pacing pulse 186 would be inhibited.

Figure 6:
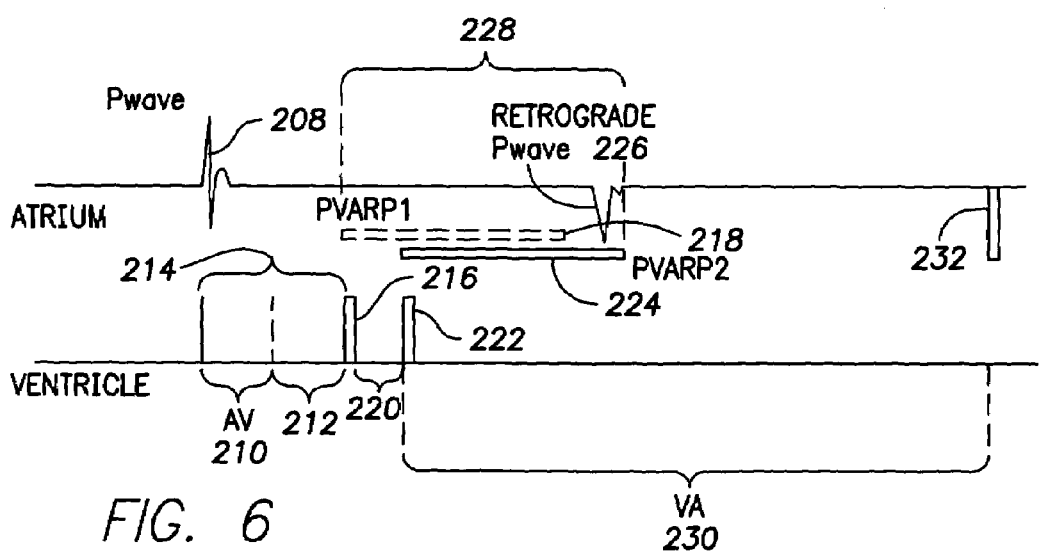
FIG. 6 is a timing diagram illustrating a first combined back-up pulse and fusion beat evaluation embodiment of the present invention.

Referring now to FIG. 6, it illustrates an embodiment wherein there is fusion beat evaluation and the delivery of a back-up pulse associated with autocapture due to true loss of capture on the primary pulse at the end of the extended AV delay. Again, a P wave 208 is sensed. Because there is fusion beat evaluation, in response to the sensed P wave 208, the timing control 79 times a lengthened AV interval 214 by timing a first AV interval 210 and then an additional VV interval 212. The effectively extends the AV interval 214, the ventricular pulse generator 72 issues a primary pacing pulse 216.

In response to the lengthened AV interval 214, upon delivery of the primary pacing pulse 216, the refractory circuit 75 begins timing a first PVARP 218. The evoked response detector 71 fails to detect an evoked response from primary pacing pulse 216 to cause the timing control 79 to begin timing delivery of the back-up ventricular pulse effectively inducing a further extension of the AV interval by 60 to 100 ms identified by interval 220. At the end of the extension interval 220, the ventricular pulse generator 72 delivers a back-up pacing pulse 222. In response to the back-up pacing pulse 222, the refractory circuit 75 begins the timing of a second PVARP 224. The second PVARP 224 may have the same duration as the first PVARP 218 or may be of greater duration than the first PVARP 218.

Because of the effectively lengthened AV interval from the P wave 218 to the deliver of the back-up pulse 222, the atria are provided sufficient time to recover to permit the ventricular depolarization caused by the back-up pulse 222 to be retrogradedly conducted causing a retrograde P wave 226. However, by virtue of the lengthened PVARP 228, the retrograde P wave 226 occurs during the lengthened PVARP. As a result, the retrograde P wave 226 is not tracked by the device to prevent a potential PMT. Again, the timing control 79 times a VA interval 230 from the back-up pulse 222 to cause the atrial pulse generator 72 to deliver an atrial pacing pulse 232 at the end of the VA interval 230. Again, should a P wave be sensed after the extended PVARP 228 but before the end of the VA interval 230, the timing control 79 will begin timing a new AV interval from the sensed P wave and the atrial pacing pulse 232 will be inhibited.

Figure 7:
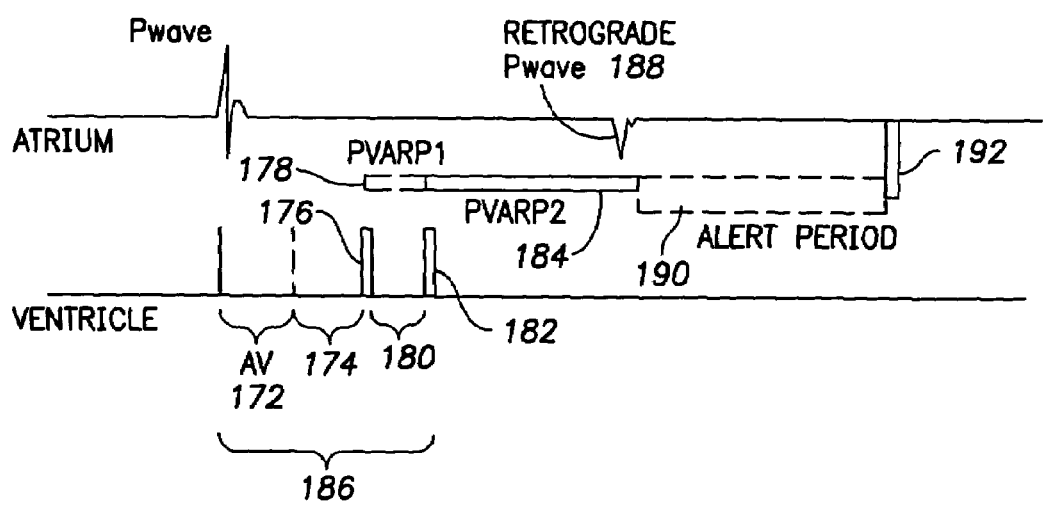
FIG. 7 is a timing diagram illustrating a further combined back-up pulse and fusion beat evaluation embodiment of the present invention.

Referring now to FIG. 7, it illustrates another embodiment wherein there is fusion beat evaluation and delivery of a back-up pulse during autocapture. Here, again, a P wave 170 is sensed. Because ventricular fusion beat evaluation is to be conducted, the timing control 79 times a first AV interval 172 and an AV interval extension 174. At the end of the AV interval extension 174, the ventricular pulse generator 72 issues a primary pacing pulse 176.

Upon delivery of the primary pacing pulse 176, the refractory circuit 75 begins the timing of a first PVARP 178. If the primary pulse is ineffective (associated with failure to detect the ER signal and hence labeled loss of capture), the timing control 79 also begins the timing for delivery of the back-up pulse 182. This functionally provides an extension 180 of the AV delay by the 60 to 100 ms.

As will also be noted in FIG. 7, the evoked response detector 71 fails to detect an evoked response to the primary pacing pulse 176 and therefore the ventricular pulse generator 72 delivers a back-up ventricular pacing pulse 182. The functional long AV delay 186 may allow for retrograde conduction. Upon delivery of the back-up pacing pulse 182, the refractory circuit 75 terminates the first PVARP 178 and immediately begins timing a second PVARP 184. The second PVARP 184 may be equal to or greater than the duration of a normal PVARP interval provided by the device.

As in the previous embodiments, the lengthened AV interval 186 is of sufficient duration to permit the atria to recover from the P wave 170. As a result, a retrograde P wave 188 occurs. However, because of the restarted PVARP, the retrograde P wave 188 occurs during the PVARP so as to not be tracked. Hence, a potential PMT is thereby prevented.

Following the second PVARP 184, the timing control 79 times an alert period 190 of fixed duration. Following the fixed period 190, the atrial pulse generator 70 delivers an atrial pacing pulse 192 to begin the next cardiac cycle.

The atrial pacing pulse 192 may be delivered at the end of the alert period 190 if a scheduled atrial pacing pulse, by virtue of a timed VA interval, (not shown) is to be provided during the extended PVARP 185. Still further, the atrial pacing pulse 192 may be provided at the end of the alert period if the scheduled atrial pacing pulse is to occur too close to the retrograde P wave 188 to permit the atria to have fully recovered from the retrograde P wave. Alternatively, the device may be programmed so that the atrial pacing pulse 192 is always delivered at the end of the alert period 190. However, regardless of when the atrial pacing pulse 192 is to be delivered, if a P wave is detected after the extended PVARP 184 and before the end of the alert period 190, it is tracked to begin a next cardiac cycle and the atrial pacing pulse 192 may be inhibited.

While the invention has been described by means of specific embodiments and applications thereof, it is understood that numerous modifications and variations may be made thereto by those skilled in the art without departing from the spirit and scope of the invention. For example, while the various embodiments herein have been described in the context of PVARP extension during autocapture, it will be appreciated by those skilled in the art that the invention may be employed to advantage in other settings as well. For example, the present invention may be employed during auto intrinsic conduction searches with AV pacing. It is therefore to be understood that within the scope of the claims, the invention may be practiced otherwise than as specifically described herein.

What is claimed is:

1. An implantable cardiac stimulation system comprising:
   a pulse generator that provides atrial and ventricular pacing stimulation pulses;
   a sensing circuit that senses atrial and ventricular activity;
   a timing control circuit that establishes an AV interval from a sensed atrial event to provision of a ventricular pacing pulse; and
   a refractory circuit that establishes a PVARP following each provided ventricular pacing pulse including a lengthened PVARP greater in duration than a normal PVARP responsive to the timing control circuit establishing a lengthened AV interval greater in duration than a normal AV interval, wherein the refractory circuit establishes the lengthened PVARP by providing a second PVARP either during a first PVARP or upon termination of a first PVARP.

2. The device of claim 1 wherein the second PVARP is longer in duration than the first PVARP.

3. The device of claim 1 wherein the refractory circuit initiates the second PVARP responsive to a back-up ventricular pacing pulse.

4. The device of claim 1 wherein the refractory circuit terminates the PVARP responsive to the sensing circuit sensing a P wave during the lengthened PVARP.

5. The device of claim 1 wherein the pulse generator provides an atrial pacing pulse a fixed interval after the lengthened PVARP.

6. The device of claim 1 wherein the refractory circuit further provides an atrial alert period following the lengthened PVARP.

7. An implantable cardiac stimulation system comprising:
   a pulse generator that provides atrial and ventricular pacing stimulation pulses;
   a sensing circuit that senses atrial and ventricular activity;
   a timing control circuit that establishes an AV interval from a sensed atrial event to provision of a ventricular pacing pulse;
   a refractory circuit that establishes a PVARP following each provided ventricular pacing pulse including a lengthened PVARP greater in duration than a normal PVARP responsive to the timing control circuit establishing a lengthened AV interval greater in duration than a normal AV interval; and a fusion beat detector that discriminates fusion associated with intact AV nodal conduction from true loss of ventricular capture and wherein the timing control circuit establishes the lengthened AV interval responsive to detection of a fusion beat.

8. An implantable cardiac stimulation system comprising:

a pulse generator that provides atrial and ventricular pacing stimulation pulses;

a sensing circuit that senses atrial and ventricular activity;

a timing control circuit that establishes an AV interval from a sensed atrial event to provision of a ventricular pacing pulse; and a refractory circuit that establishes a PVARP following each provided ventricular pacing pulse including a lengthened PVARP greater in duration than a normal PVARP responsive to the timing control circuit establishing a lengthened AV interval greater in duration than a normal AV interval;

wherein the timing control circuit further times a VA interval that schedules provision of a next atrial pacing pulse and wherein the pulse generator provides an atrial pacing pulse a fixed interval after detection of a retrograde P wave by the sensing circuit during the lengthened PVARP when the time between the retrograde P wave and the scheduled atrial pacing pulse is less than a present duration.

9. An implantable cardiac stimulation device including a pulse generator that provides atrial and ventricular pacing stimulation pulses and a sensing circuit that provides atrial and ventricular sensing, the device comprising:

timing control means for establishing an AV interval from an atrial event to provision of a ventricular pacing pulse; and refractory means for establishing a PVARP following each provided ventricular pacing pulse including a lengthened PVARP greater in duration than a normal PVARP responsive to the timing control means establishing a lengthened AV interval greater in duration than a normal AV interval;

wherein the refractory means includes means for providing a second PVARP either during a first PVARP or upon termination of a first PVARP to provide the lengthened PVARP.

10. The device of claim 9 wherein the second PVARP is longer in duration than the first PVARP.

11. The device of claim 9 wherein the refractory circuit includes means for initiating the second PVARP responsive to a back-up ventricular pacing pulse.

12. The device of claim 9 wherein the pulse generator provides an atrial pacing pulse a fixed interval after the lengthened PVARP.

13. The device of claim 9 wherein the refractory means further provides an atrial alert period following the lengthened PVARP.

14. The device of claim 13 wherein the pulse generator provides an atrial pacing pulse upon completion of the atrial alert period.

15. An implantable cardiac stimulation device including a pulse generator that provides atrial and ventricular pacing stimulation pulses and a sensing circuit that provides atrial and ventricular sensing, the device comprising:

timing control means for establishing an AV interval from an atrial event to provision of a ventricular pacing pulse;

refractory means for establishing a PVARP following each provided ventricular pacing pulse including a lengthened PVARP greater in duration than a normal PVARP responsive to the timing control means establishing a lengthened AV interval greater in duration than a normal AV interval; and a fused beat detecting means for detecting a ventricular fused beat and wherein the timing control means establishes the lengthened AV interval responsive to detection of a fused beat.

16. The device of claim 15 wherein the refractory means terminates the PVARP responsive to the sensing circuit sensing a P wave during the lengthened PVARP.

17. The device of claim 16 wherein the pulse generator provides an atrial pacing pulse a fixed time after sensing of the P wave.

* * * * *